United States Patent [19]
Ogle

[11] Patent Number: 5,935,077
[45] Date of Patent: Aug. 10, 1999

[54] NONINVASIVE BLOOD FLOW SENSOR USING MAGNETIC FIELD PARALLEL TO SKIN

[76] Inventor: John Seldon Ogle, 1472 Pashote Ct., Milpitas, Calif. 95035

[21] Appl. No.: 08/911,421

[22] Filed: Aug. 14, 1997

[51] Int. Cl.⁶ ........................................... A61B 5/02
[52] U.S. Cl. ........................... 600/504; 73/861.12
[58] Field of Search .................... 600/407, 409, 600/454, 468, 504–505, 465; 73/861.12

[56] References Cited

U.S. PATENT DOCUMENTS

| | | |
|---|---|---|
| 3,759,247 | 9/1973 | Doll et al. . |
| 4,412,545 | 11/1983 | Okino ........................................ 128/691 |
| 4,676,253 | 6/1987 | Newman et al. ......................... 600/505 |
| 4,727,754 | 3/1988 | Rukel .................................... 73/861.12 |
| 4,881,413 | 11/1989 | Georgi et al. ......................... 73/861.12 |
| 5,220,841 | 6/1993 | Brown ................................... 73/861.12 |
| 5,598,841 | 2/1997 | Tanji et al. ............................. 600/342 |
| 5,865,749 | 2/1999 | Doten et al. ............................. 600/443 |

OTHER PUBLICATIONS

Hiroshi Kanai, Eiki Yamano, Kiyoshi Nakayama, Naoshige Kawamura, and Hiroshi Furuhata; IEEE Transactions on Biomedical Engineering, vol. BME–21, No. 2, Mar. 1974; Transcutaneous Blood Flow Measurement by Electromagnetic Induction; Mar. 01, 1974; 8 pgs.

*Primary Examiner*—Jeffrey R. Jastrzab
*Assistant Examiner*—Ryan Carter

[57] ABSTRACT

An improved electromagnetic blood flow sensor uses a bipolar magnetic field source to provide a varying magnetic field with a component parallel to the skin and through the blood vessel, a single sense electrode on the skin adjacent to the blood vessel, a reference electrode, and a detector that samples the sense electrode signal in synchronism to the varying magnetic field. An optional addition is a driven shield for the sense electrode to reduce the effect of noise voltages either from the magnetic field source or from stray fields.

11 Claims, 5 Drawing Sheets

NONINVASIVE BLOOD FLOW SENSOR USING MAGNETIC FIELD PARALLEL TO SKIN

BACKGROUND—FIELD OF INVENTION

This invention relates to noninvasive electromagnetic blood flow measurement devices, specifically to devices using an improved electrode and magnetic field configuration.

BACKGROUND—DESCRIPTION OF PRIOR ART

Measurements of blood flow characteristics are valuable in both medical research and treatment, especially measurements showing the blood flow waveform throughout a pulse cycle.

Rough noninvasive measurements of blood flow are presently made using doppler techniques, where ultrasonic sound waves are transmitted through the skin roughly parallel to the blood flow direction, and the change in sound transit time due to blood flow is used to determine the blood flow velocity. While this technique is useful, it has several inherent limitations. The measurement provides blood flow velocity, typically in meters/second, rather than the desired blood flow quantity, typically in liters/second. In addition, signal-to-noise considerations limit the accuracy of the measurement.

Accurate blood flow sensing can be achieved through invasive means as described in U.S. Pat. No. 5,220,841, Brown et al., "Electromagnetic Fluid Flow Transducer", by cutting the blood vessel and routing the blood flow through an external blood flow sensor using an electromagnetic flowmeter. While this method is accurate, it is expensive and inconvenient, so its use is normally limited to research or for operations with special sensing requirements.

Such invasive electromagnetic blood flowmeters operate by passing a magnetic field through a tube containing the blood flow and sensing the transverse voltage generated by the blood in passing through this magnetic field.

Invasive electromagnetic blood flow probes are also designed to fit around blood vessels as described in U.S. Pat. No. 4,727,754, Ruckel, "Electromagnetic Flowmeter". Such probes are available in a range of sizes to provide a snug fit around the blood vessel to be measured. Varying magnetic fields and synchronous signal detection are used to improve signal-to-noise ratios.

U.S. Pat. No. 4,412,545, Okino et al., "Electromagnetic Blood Flowmeter" describes more sophisticated signal processing to further improve signal-to-noise ratios.

While the technique of using a blood flow sense probe around the blood vessel is preferable to cutting the blood vessel and installing a flow sensor in the blood flow path, it still involves cutting through the skin so the sensor can be mounted around the blood vessel. A truly noninvasive approach, avoiding any physical disruption of the skin, can be achieved by generating an external varying magnetic field, directing it through the skin and the blood vessel, and measuring that part of the electric field resulting from blood flow that is available at the skin. This type of noninvasive measurement is called transcutaneous.

Present noninvasive electromagnetic blood flow sensors have poor signal-to-noise ratios because only a small portion of the magnetic field energy generated external to the skin couples through the blood vessel and only a small portion of the electric field generated by the blood flow through this magnetic field appears at the skin surface. The result is limited accuracy and excessive sensitivity to noise and motion artifacts.

A typical noninvasive blood flow measurement development project is described in the report titled "Transcutaneous Blood Flow Measurement by Electromagnetic Induction", by Hiroshi Kanai, Eiki Yamano, Kiyoshi Nakayama, Naoshige Kawamura, and Hiroshi Furuhata, printed in IEEE Transactions on Biomedical Engineering, Vol BME-21, No. 2, March 1974.

For this development a magnetic unipole placed adjacent to the blood vessel to be measured is excited at 400 Hz, and a difference voltage from electrodes on the skin surface at opposite sides of the blood vessel provides a signal amplitude proportional to the blood flow. Noise signals at the 400 Hz excitation frequency are balanced out as well as possible and the remaining alternating difference signal is amplified and then detected by a circuit which includes two phase sensitive detectors and a balanced modulator, to provide the desired blood flow signal.

For this configuration the varying magnetic field is mainly perpendicular to the skin, so the blood flow sense signal is parallel to the skin. Since the flesh adjacent to the blood vessel has a resistivity comparable to the resistivity of the blood, the electrical signal resulting from blood flow is attenuated with distance from the blood vessel. For maximum difference signal amplitude the electrode spacing is approximately equal to twice the distance from the skin to the blood vessel. Thus the optimum distance from each electrode to the blood vessel is approximately equal to the square root of two times the distance from the blood vessel to the skin.

With this high impedance differential electrode arrangement near the stray electrical fields from the varying electromagnetic field source, there are severe common mode noise problems.

As is stated in the report "There are many difficulties to be overcome in the transcutaneous measurement of blood flow by electromagnetic induction, especially electrostatic, leakage resistance, and electromagnetic coupling between the detecting and exciting circuits".

OBJECTS AND ADVANTAGES

Accordingly, several objects and advantages of my invention are to provide noninvasive blood flow measurements of more accuracy than with presently available noninvasive electromagnetic blood flow sensors, and to make multiple measurements available to allow simultaneous comparison of blood flows at different points in the body.

Still further objects and advantages will become apparent from a consideration of the ensuing description and accompanying drawings.

Figure 1:
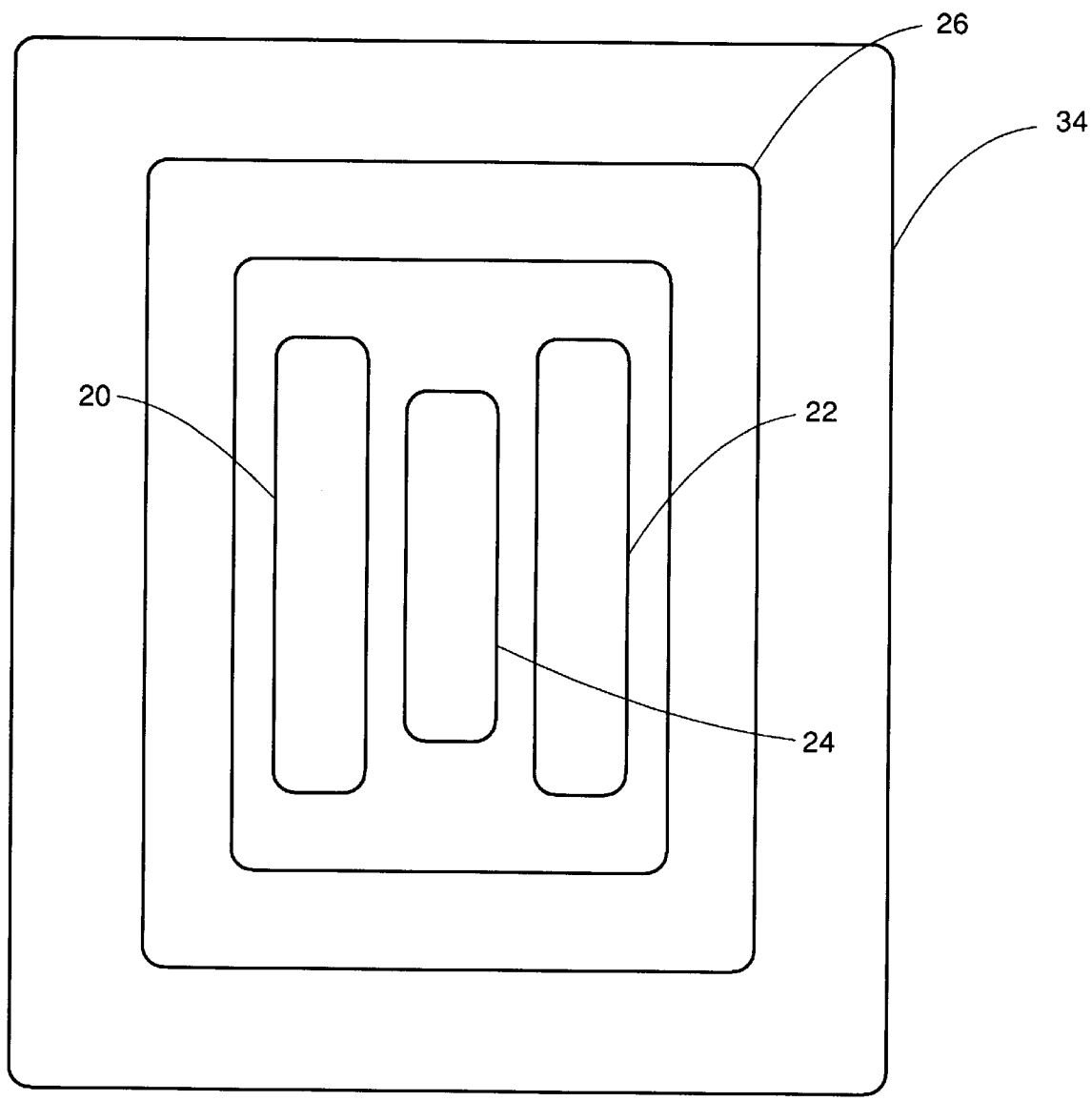
FIG. 1 is a view of the bottom of the probe showing the components of the probe which are adjacent to the skin.

REFERENCE NUMERALS 10 blood vessel
12 skin
14 first coil
16 second coil
18 ferromagnetic U core
20 varying magnetic pole
22 opposite polarity varying magnetic pole
24 sense electrode
26 reference electrode
28 varying magnetic flux
30 sense electrode shield
32 reference electric shield
34 blood flow probe
36 square wave coil driving voltage
38 varying magnetic field waveform
58 driver coupling transformer
60 signal coupling transformer
62 coil drive and synchronizing signal source
64 driver and signal processing enclosure
72 cable
76 carrier frequency amplifier
86 sense electrode buffer amplifier
92 reference electrode buffer amplifier
94 first timing pulse waveform
96 first sample and hold circuit
98 second sample and hold circuit
100 third sample and hold circuit
102 second timing pulse waveform
104 third timing pulse waveform
106 differential amplifier
114 amplified signal
116 plus output voltage
118 minus output voltage

SUMMARY

A noninvasive electromagnetic blood flow measurement system comprises a probe containing two opposite polarity varying magnetic poles, a sense electrode located between the magnetic poles, and a reference electrode located away from the magnetic poles; amplification for the difference electrical voltage between the sense electrode and the reference electrode, electrical shields for the sense electrode, an electric energy source driving the varying magnetic poles, and a sampling detection means synchronous to the electric energy source waveform driving the varying magnetic poles.

Preferred Embodiment—Description

FIG. 1 is a bottom view of probe 34 showing the components adjacent to skin 12.

Figure 2:
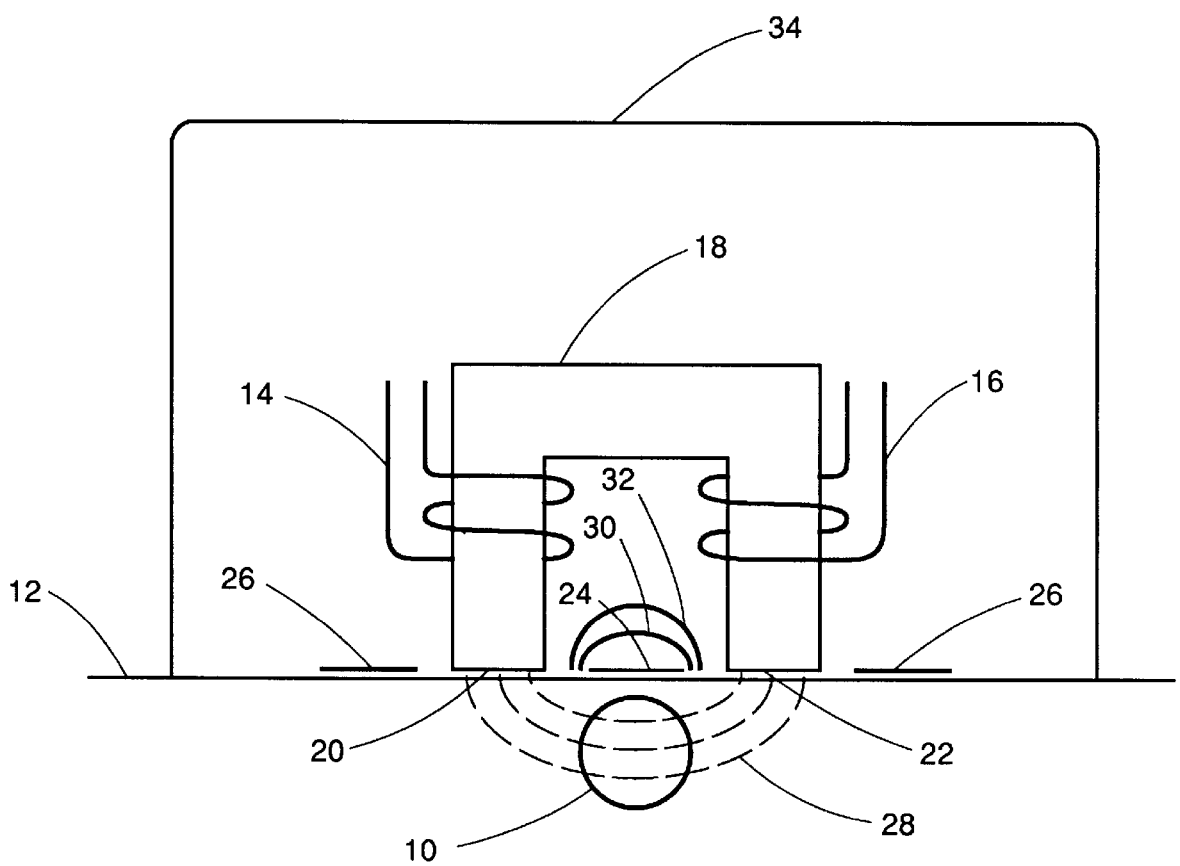
FIG. 2 is a cross sectional view showing the locations of the components inside the probe and the positioning of the probe relative to the blood vessel.

FIG. 2 is a cross sectional view showing the locations of the components in blood flow probe 34 relative to skin 12 and blood vessel 10.

Figure 3:
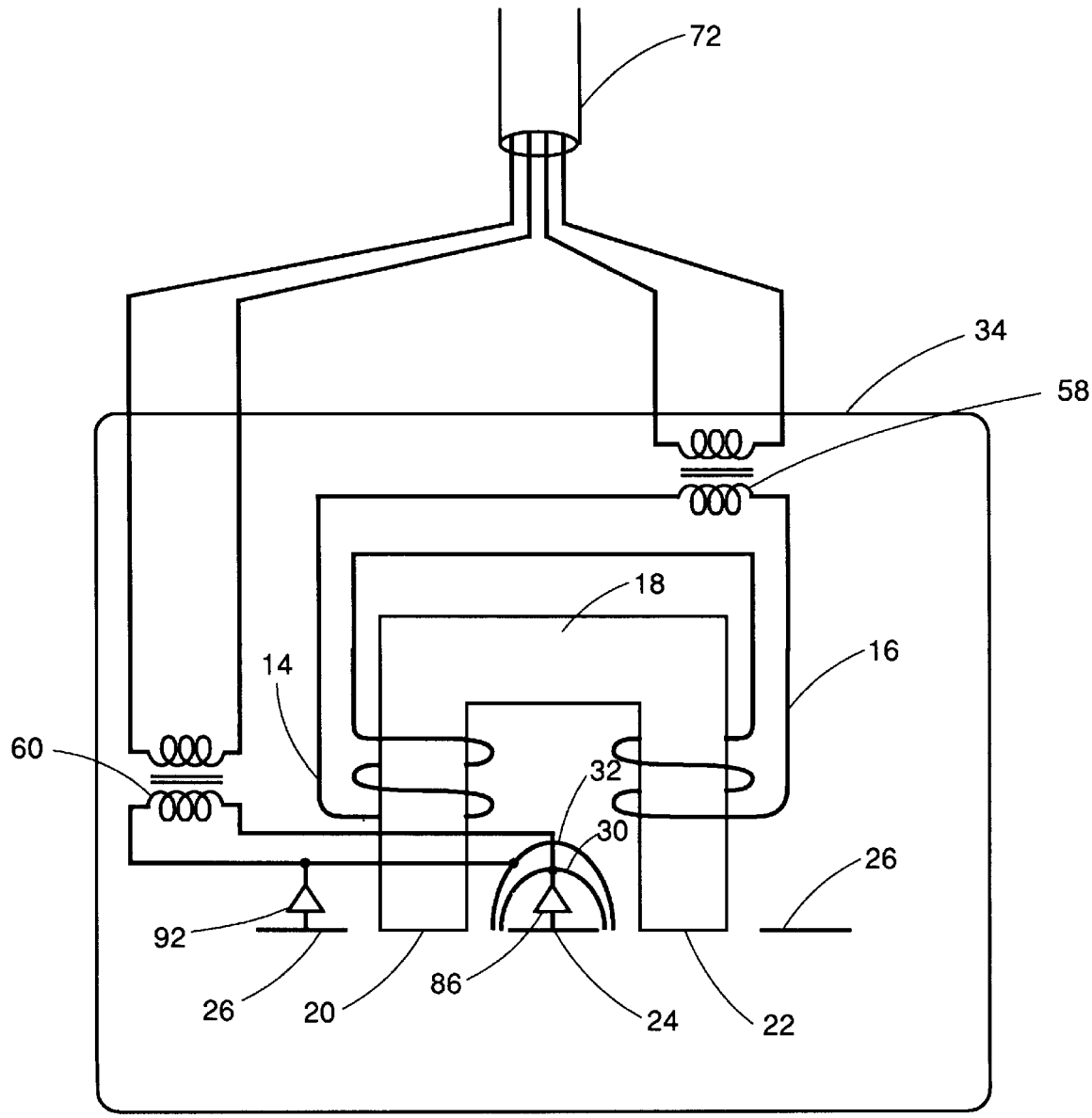
FIG. 3 is a simplified electronic schematic diagram of a preferred version of the probe portion of my invention.

FIG. 3 is a simplified electronic schematic of the circuits in blood flow probe 34.

Figure 4:
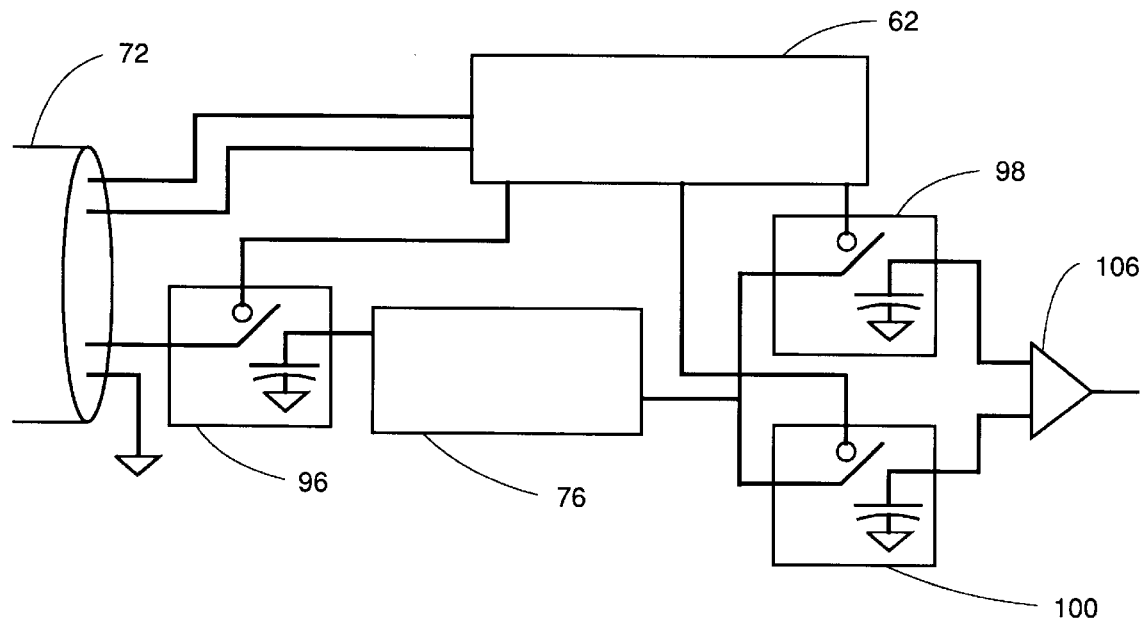
FIG. 4 is a block diagram showing the signal processing and coil driving circuits of a preferred version of my invention

FIG. 4 is a block diagram showing signal processing and coil driving circuits in driver and signal processing enclosure 64.

Figure 5:
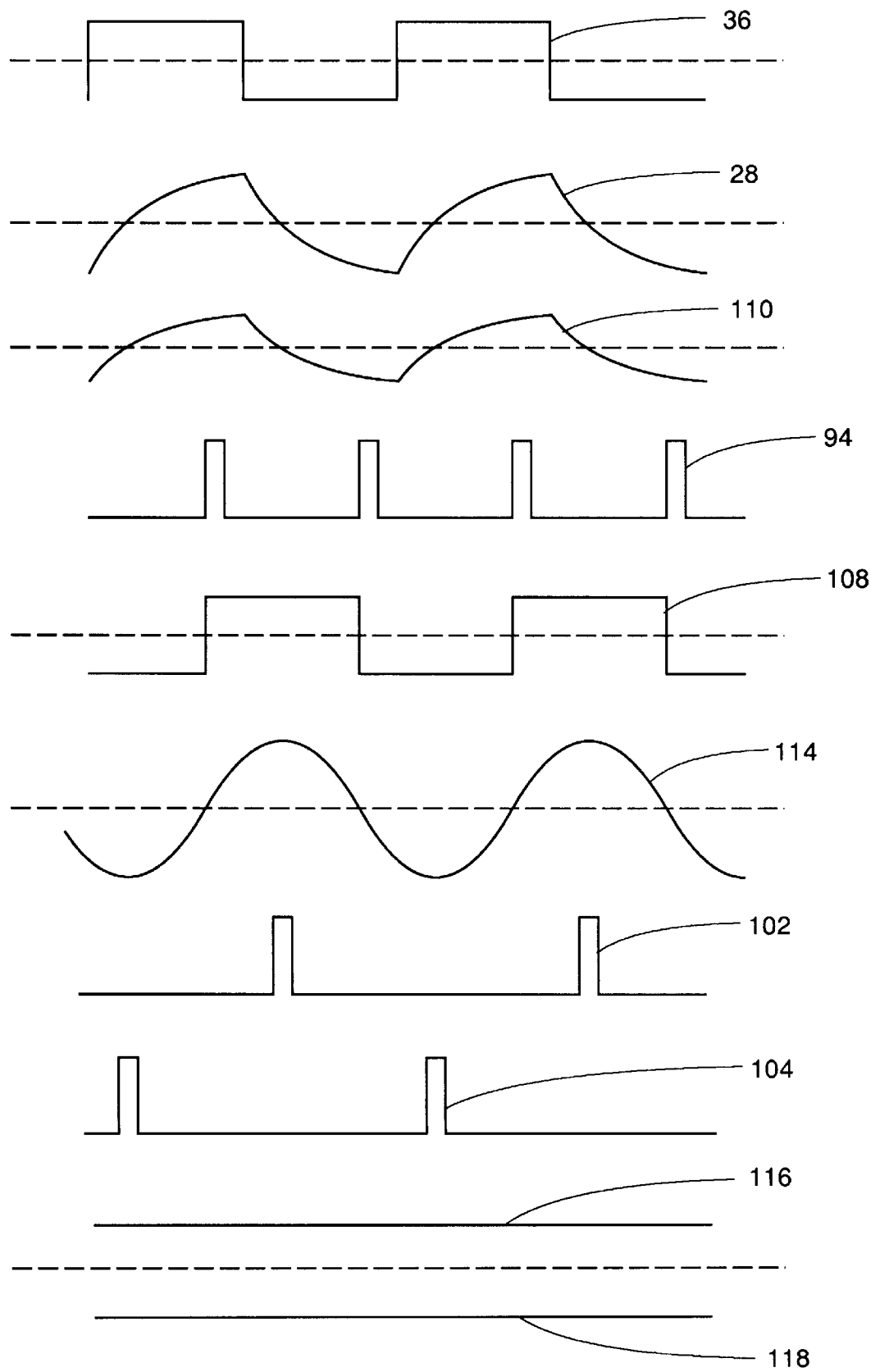
FIG. 5 is a representative series of voltage waveforms over two varying magnetic flux cycles.

FIG. 5 shows representative waveforms over two varying magnetic flux cycles.

FIG. 1 is a bottom view of blood flow probe 34, showing the components adjacent to skin 12. Sense electrode 24 is a metal plate at the center of the bottom of blood flow probe 34, with varying magnetic pole 20 on one side of sense electrode 24 and opposite polarity varying magnetic pole 22 on the opposite side of sense electrode 24. Reference electrode 26 is a metal plate surrounding varying magnetic pole 20, opposite polarity varying magnetic pole 22, and sense electrode 24.

FIG. 2 is a cross sectional view showing the locations of the components in blood flow probe 34 relative to skin 12 and blood vessel 10. Blood flow probe 34 is placed so that sense electrode 24 is either in direct contact with or capacitively coupled to skin 12 directly above blood vessel 10. Varying magnetic pole 20 and opposite polarity varying magnetic pole 22 generate varying magnetic flux 28, which extends below skin 12 and through blood vessel 10. Blood flow in blood vessel 10 through varying magnetic flux 28 generates an instantaneous blood flow source signal voltage between the top of blood vessel 10 near skin 12 and the bottom of blood vessel 10. This instantaneous blood flow source signal voltage is proportional to the product of the blood flow and varying magnetic flux 28.

A portion of the instantaneous blood flow source signal voltage is coupled from the top of blood vessel 10, through skin 12, and appears on sense electrode 24 as a blood flow signal voltage.

FIG. 3 is a simplified electric schematic diagram of the circuits in blood flow probe 34. Square wave coil driving voltage 36 from driver and signal processing enclosure 64 is connected through cable 72 to the primary winding of driver coupling transformer 58, and the secondary of driver coupling transformer 58 powers first coil 14 and second coil 16. Electric current flowing through first coil 14 and second coil 16 generate varying magnetic pole 20 and opposite polarity varying magnetic pole 22, resulting in varying magnetic flux 28, which passes through blood vessel 10.

The output of sense electrode buffer amplifier 86 is a low impedance voltage equal to the blood flow signal voltage on sense electrode 24. This low impedance voltage drives sense electrode shield 30 and one side of the primary winding of signal coupling transformer 60.

Blood flow probe 34 is placed so that reference electrode 26 is also in direct contact with or capacitively coupled to skin 12, but in an area away from varying magnetic flux 28. The output of reference electrode buffer amplifier 92 is a low impedance voltage equal to the voltage on reference electrode 26. This low impedance voltage drives reference electric shield 32 and the other side of the primary winding of signal coupling transformer 60.

The voltage on the secondary of signal coupling transformer 60 is the probe output voltage 110, and is proportional to the difference between the voltage on sense electrode 24 and the voltage on reference electrode 26. This probe output voltage 110 is coupled through cable 72 to driver and signal processing enclosure 64.

FIG. 4 is a block diagram showing a preferred version of the coil driving and signal processing circuits located in driver and signal processing enclosure 64. Coil drive and synchronizing signal source 62 generates square wave coil driving voltage 36, which is connected through cable 72 to driver coupling transformer 58 in blood flow probe 34. Coil drive and synchronizing signal source 62 also generates first timing pulse waveform 94, second timing pulse waveform 102, and third timing pulse waveform 104.

Probe output voltage 110 is the signal input to first sample and hold circuit 96, which is enabled by first timing pulse waveform 94. The output of first sample and hold circuit 96 is square wave signal 108.

Carrier frequency amplifier 76 is tuned to the frequency of square wave coil driving voltage 36, and amplifies the fundamental signal frequency of square wave signal 108. The output of carrier frequency amplifier 76 is amplified signal 114, which provides signal input to second sample and hold circuit 98 and third sample and hold circuit 100.

Second timing pulse waveform 102 enables second sample and hold circuit 98, and third timing pulse waveform 104 enables third sample and hold circuit 100. The output of second sample and hold circuit 98 is plus output voltage 116, and the output of third sample and hold circuit 100 is minus output voltage 118. Plus output voltage 116 and minus output voltage 118 have opposite polarities and are approximately equal, varying in amplitude with blood flow. The voltage difference between plus output voltage 116 and minus output voltage 118 is amplified and buffered in differential amplifier 106. The output of differential amplifier 106 is the desired voltage proportional to the blood flow.

FIG. 5 shows the time relationship between the drive, signal, and timing pulse waveforms for two cycles of square wave coil driving voltage 36.

Square wave coil driving voltage 36 drives current through first coil 14 and second coil 16. The inductive reactance and resistance in these coils results in the waveform of varying magnetic flux 28.

Probe output voltage 110 is proportional to the product of the blood flow and varying magnetic flux 28.

First timing pulse waveform 94 causes first sample and hold circuit 96 to sample and hold immediately before each transition in square wave coil driving voltage 36. Thus the output of first sample and hold circuit 96 is square wave signal 108 with frequency equal to the frequency of square wave coil driving voltage 36 and amplitude proportional to probe output voltage 110. Carrier frequency amplifier 76 is tuned to the frequency of square wave coil driving voltage 36, and amplifies the fundamental frequency component of square wave signal 108.

The output of carrier frequency amplifier 76 is amplified signal 114, which is applied to the signal inputs of second sample and hold circuit 98 and third sample and hold circuit 100.

Second timing pulse waveform 102 has a sampling pulse intermediate between the two sampling pulses of first timing pulse waveform 94 corresponding to a negative value of square wave coil driving voltage 36, and controls sampling of second sample and hold circuit 98.

Third timing pulse waveform 104 has a sampling pulse intermediate between the two sampling pulses of first timing pulse waveform 94 corresponding to a positive value of square wave coil driving voltage 36, and controls third sample and hold circuit 100.

The output of second sample and hold circuit 98 is plus output voltage 116, with amplitude proportional to amplified signal 114. The output of third sample and hold circuit 100 is minus output voltage 118, with amplitude also proportional to amplifiedsignal 114.

The voltage difference between plus output voltage 116 and minus output voltage 118 is amplified in differential amplifier 106. The output of differential amplifier 106 is the desired blood flow signal.

Preferred Embodiment—Operation

The Blood Flow Sense Probe is placed against the skin over the blood vessel to be measured. The sensed blood flow is displayed and/or made available to external display or external processing equipment.

Other Embodiments
Direct Synchronous Detection—Description

A simpler synchronous detection arrangement is to demodulate the blood flow signal directly, without using a carrier amplifier. In this case the modulated blood flow signal is fed into two sample and hold circuits, one of which is sampled just before the positive transition of the coil drive voltage and the other is sampled just before the negative transition of the coil drive voltage. The two resulting voltages are amplified in a differential amplifier, and the output of this amplifier is the blood flow signal.

Probe Mounted Coil Driver—Description

In order to reduce potential noise coupling in cable 72, direct current power can be used rather than square wave coil driving voltage 36 from driver and signal processing enclosure 64 to blood flow probe 34, and a coil driving circuit controlled by an RS flip flop can be incorporated in blood flow probe 34. Synchronization can be accomplished by including two low level synchronization lines in cable 72 from driver and signal processing enclosure 64 to the RS flip flop.

Synchronous Detector using Analog Multiplier—Description

An analog multiplier can be used in place of sample and hold circuits for synchronous detection.

Conclusions, Ramifications, and Scope

Accordingly, it can be seen that an electromagnetic blood flow sensor with improved accuracy has been described, with reduced susceptibility to electromagnetic noise. The use of a bipolar magnetic field source enables a larger and more uniform magnetic field through a blood vessel. The use of a single sense electrode adjacent to the blood vessel in conjunction with a reference electrode provides a larger sense signal. The use of synchronous detection of the sense signal reduces the effect of electrical noise from power line and other non synchronous signals, as well as assuring that electrical field transients from the bipolar magnetic field source are minimized when the sense signal is sampled. The use of a driven shield for the sense electrode also reduces noise coupling from the bipolar magnetic field source.

Although the description above contains many specificities, these should not be construed as limiting the scope of the invention but as merely providing illustrations of some of the presently preferred embodiments of this invention. Various other embodiments and ramifications are possible within it's scope. Thus the scope of the invention should be determined by the appended claims and their legal equivalents, rather than by the examples given.

What is claimed is:

1. An apparatus for noninvasive measurement of blood flow, comprising:

A probe incorporating two varying magnetic field poles of opposite polarity mounted near the bottom surface of said probe so that when said probe is placed adjacent to the skin there is a component of varying magnetic flux extending beneath and parallel to said skin;

An electrical field sense electrode mounted on the bottom of said probe between said opposite polarity varying magnetic field poles so that when said probe is placed adjacent to said skin said electrical field sense electrode is in contact with or capacitively coupled to said skin;

An electrical field reference electrode placed in contact with or capacitively coupled to said skin and removed from the area of varying magnetic flux generated by said varying magnetic field poles; and Synchronous detection electric circuitry which samples the voltage difference between said electrical field sense electrode and said electrical field reference electrode at two or more times during each cycle of said varying magnetic field, and provides an output voltage related to the variation of said voltage difference corresponding to said varying magnetic field.

2. The apparatus of claim 1, wherein:

Said synchronous detection electric circuitry consists of a first sample and hold circuit sampled twice each cycle of said opposite polarity varying magnetic field poles, providing a square wave voltage with peak-to-peak voltage related to the magnitude of said blood flow;

a carrier frequency amplifier which operates at the frequency of said opposite polarity varying magnetic poles and provides an amplified voltage corresponding to the amplitude of the fundamental frequency of said square wave voltage;

second sample and hold circuit and third sample and hold circuit which alternately sample said amplified voltage at each half cycle of said variable magnetic field pole; and additional filtering and amplification of the difference between the outputs of said second sample and hold circuit and said third sample and hold circuit.

3. The apparatus of claim 1, wherein:

said opposite polarity varying magnetic field poles comprise one or more coils; and a varying electrical energy source drives electric current through said coils.

4. The apparatus of claim 3, wherein:

said opposite polarity varying magnetic field poles comprise a U cross-section ferromagnetic core with two coils, one of said coils wound around each leg of said U cross-section ferromagnetic core; and a varying electrical energy source driving electric current through said coils.

5. The apparatus of claim 3, wherein:

said varying electrical energy source provides square wave voltages across said coils.

6. The apparatus of claim 3, wherein:

said electrical energy source is transformer coupled to said coils.

7. The apparatus of claim 1, wherein:

A driven electric shield is mounted adjacent to said electric field sense electrode, surrounding said electric field sense electrode except for the side of said electric field sense electrode adjacent to said skin; and a sense electrode voltage follower amplifier with input voltage from said electric field sense electrode and output voltage driving said driven electric shield and providing an output signal.

8. The apparatus of claim 7, wherein:

A reference electric shield is mounted adjacent to said driven electric shield on the side of said driven electric shield away from said electric field sense electrode; and a reference electrode voltage follower amplifier with input voltage from said electric field reference electrode has output voltage driving said reference electric shield.

9. The apparatus of claim 1, wherein:

Multiple electromagnetic noninvasive blood flow measurement probes and associated electronics are combined in one measurement system.

10. The apparatus of claim 7, wherein:

the difference between the output of said sense electrode voltage follower amplifier and said reference electrode voltage follower amplifier is transformer coupled to said synchronous detection electrical circuitry.

11. A method for using the apparatus of claim 1, wherein:

Said noninvasive blood flow measurement probe is placed adjacent to said skin so that said electric field sense electrode is adjacent to said blood vessel and said varying magnetic field is at approximately a right angle to said blood vessel;

the voltage from said synchronous detector is filtered to form a blood flow voltage signal related to the magnitude of blood flow through said blood vessel; and said blood flow voltage signal is either displayed or applied to additional equipment for further processing.

* * * * *